United States Patent
Matsuzaki

Patent Number: 5,303,033
Date of Patent: Apr. 12, 1994

[54] GRADIENT INDEX MEASURING APPARATUS

[75] Inventor: Hiroshi Matsuzaki, Hachiouji, Japan

[73] Assignee: Olympus Optical Co., Ltd., Tokyo, Japan

[21] Appl. No.: 978,334

[22] Filed: Nov. 18, 1992

[30] Foreign Application Priority Data

Nov. 19, 1991 [JP] Japan .................... 3-302911

[51] Int. Cl.⁵ .................................. G01B 9/02
[52] U.S. Cl. .......................... 356/345; 356/361
[58] Field of Search ........... 356/345, 359, 360, 361

[56] References Cited

U.S. PATENT DOCUMENTS 4,842,408 6/1989 Yoshii et al. .................... 356/349

FOREIGN PATENT DOCUMENTS 62-263428 11/1987 Japan .

OTHER PUBLICATIONS

Univ. of Electrocommunications, "Subfringe Interferometry Fundamentals," Mitsuo Takeda, Oct. 1983 pp. 55-65.
Homogeneity testing by phase sampling interferometry, Johannes Schwider et al, Sep. 15, 1985/vol. 24, No. 18 Applied Optics pp. 3059-3061.

Primary Examiner—Samuel A. Turner
Assistant Examiner—Robert Kim
Attorney, Agent, or Firm—Cushman, Darby & Cushman

[57] ABSTRACT

A gradient index measuring apparatus includes a device for generating a first light beam and a second light beam having coherence, a sample provided on a first optical path along which the first light beam travels, a device for combining the first light beams traveling along the first optical path, transmitted through the sample, with the second light beam traveling along a second optical path, and a device for measuring interference fringes produced by the combination of the first and second light beams to calculate a gradient index of the sample from its measured value. Thus, the gradient index measuring apparatus is capable of measuring the gradient index provided in a radial direction in particular, with a high grade of accuracy, of a gradient index lens, and allows the measurement of asymmetry of the gradient index. Whereby, the quality of the measured sample is determined and the information of the measured asymmetry can be used as tolerance data in the design.

2 Claims, 3 Drawing Sheets

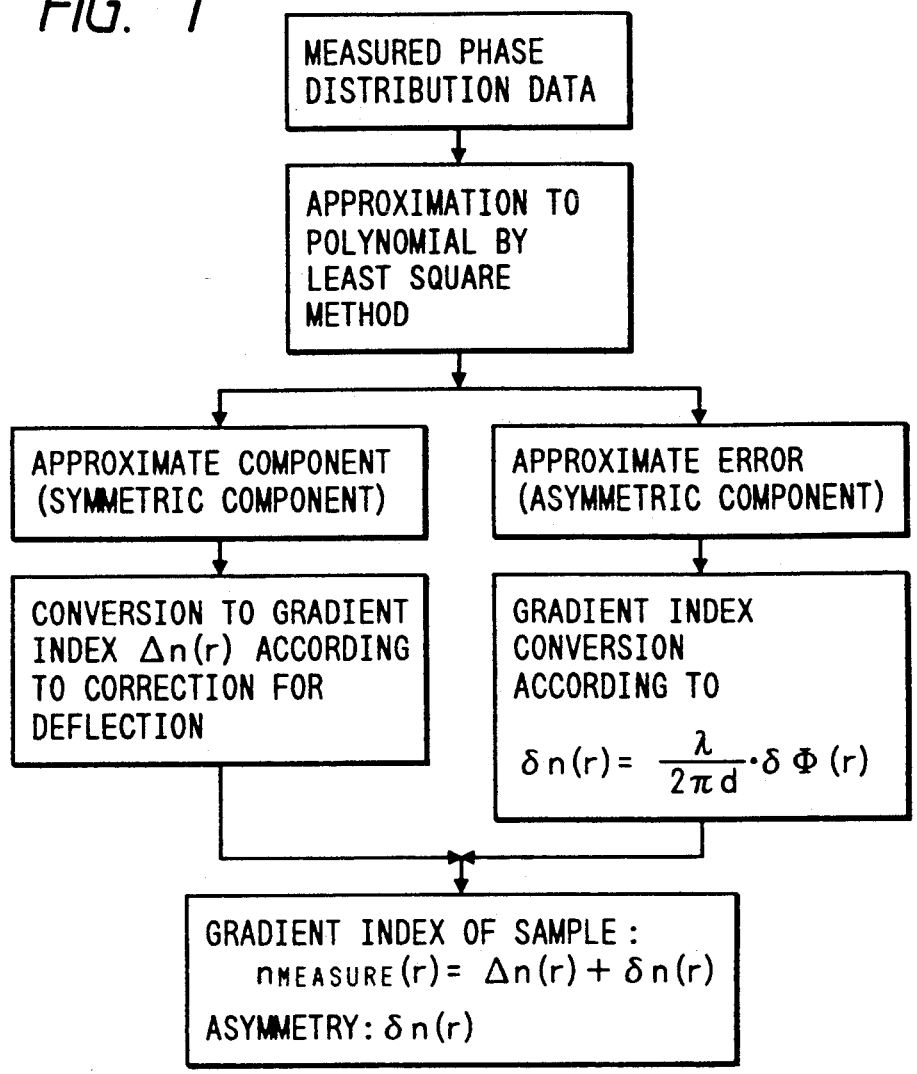
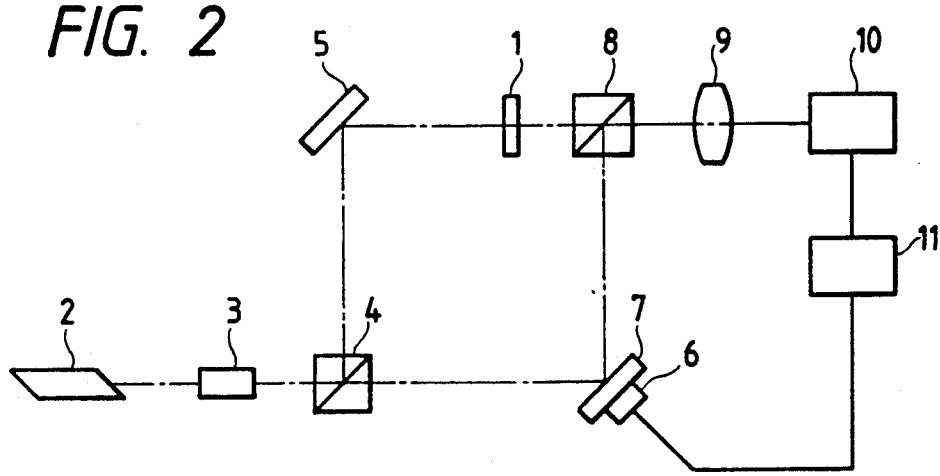

GRADIENT INDEX MEASURING APPARATUS

BACKGROUND OF THE INVENTION a) Field of the Invention:

This invention relates to a gradient index measuring apparatus utilizing the interference of light waves for measuring the gradient index of a sample and, more particularly, to an apparatus for measuring the asymmetry of the gradient index in a gradient index lens.

b) Description of the prior art:

In the past, where an interferometer is used to measure the gradient index of a sample, a method has been adopted that, as set forth in U.S. Pat. No. 4,842,408, the contour of interference fringes caused by the gradient index of the sample is measured and, based on the resultant information of phase distribution, a reduced equation is used to calculate the gradient index. The gradient index measured by such a method involves a conversion error and consequently, it is necessary to take account of the error as a tolerance in designing an optical system using a gradient index optical element on the basis of the measured value. In the prior art, when an optical system is designed in which an optical element having the gradient index radically, namely, concentrically in particular, is employed as a lens, consideration should be taken of, in addition of the tolerance, the influence of the asymmetry of the gradient index caused about the center of the lens on its properties. However, the method and apparatus for measuring the asymmetry of the gradient index have been unavailable in the past.

For inhomogeneity, an apparatus is known for measuring the inhomogeneity of a refractive index in homogeneous glass (strictly speaking, it also has inhomogeneity), for instance. This apparatus is such that homogeneous glass, both surfaces of which are ground into parallel plane surfaces, is placed in the interferometer, the parallel plane surfaces are normally irradiated with light, and the interference fringes of wave fronts of the transmitted light are observed, thereby measuring the inhomogeneity [J. Schwider et al., APPLIED OPTICS, Vol. 24, No. 18, pp. 3059-3061 (1985)]. According to the apparatus, the inhomogeneity of the sample can be measured in which the refractive index is not distributed homogenously. However, the interference fringes caused by the wave fronts transmitted through the homogenous glass merely represent a state of the deflection of light attributable to the inhomogeneity, whereas those appearing in measuring the sample with the gradient index include the information on the gradient index, such as a phase shift attributable to the thickness of the sample, as well as on the inhomogeneity of the refractive index. Hence, such interference fringes cannot bring about only the information on the inhomogeneity of the refractive index, that is, on the asymmetry of the gradient index. Since the proper method and apparatus for measuring the asymmetry of the gradient index have been unavailable, the quality of the sample has been unable to be determined in the measurement of the gradient index or the design.

SUMMARY OF THE INVENTION

It is, therefore, an object of the present invention to provide a gradient index measuring apparatus which is peculiarly suitable for measuring the gradient index, provided in a radical direction, of a gradient index lens and at the same time, capable of measuring the asymmetry of the gradient index.

To achieve this object, the gradient index measuring apparatus according to the present invention is constructed so that the data of phase distribution measured are approximated to a polynomial for phase distribution and separated into an approximate component and an approximate error component, which are each converted to the gradient index and then are added to each other to find the gradient index. Further, from the approximate error component calculated by approximating the measured phase distribution data to the phase distribution polynomial, the asymmetry of the gradient index is measured.

According to the present invention, the gradient index measuring apparatus includes means for generating a first light beam and a second light beam having coherence, a sample placed on a first optical path along which the first light beam travels, means for combining the first light beam traveling along the first optical path, transmitted through the sample, with the second light beam traveling along a second optical path, arithmetic means for measuring interference fringes produced by the combination of the first light beam with the second light beam to calculate the gradient index of the sample from its measured value.

Further, according to the present invention, the foregoing arithmetic means is equipped with means for approximating the phase distribution data derived from the interference fringes to the phase distribution polynomial, means for separating the data into the approximate component and the approximate error component, means for converting each component to the gradient index, and means for adding both converted values.

This and other objects as well as the features and advantages of the present invention will become apparent from the following detailed description of the preferred embodiment when taken in conjunction with the accompanying drawings.

BRIEF DESCRIPTION OF THE DRAWINGS

FIG. 1 is a diagram for explaining a consideration as to how the gradient index is obtained in the present invention;

FIG. 2 is a schematic view showing the optical system of an embodiment of the present invention;

DETAILED DESCRIPTION OF THE PREFERRED EMBODIMENT

Figure 3:
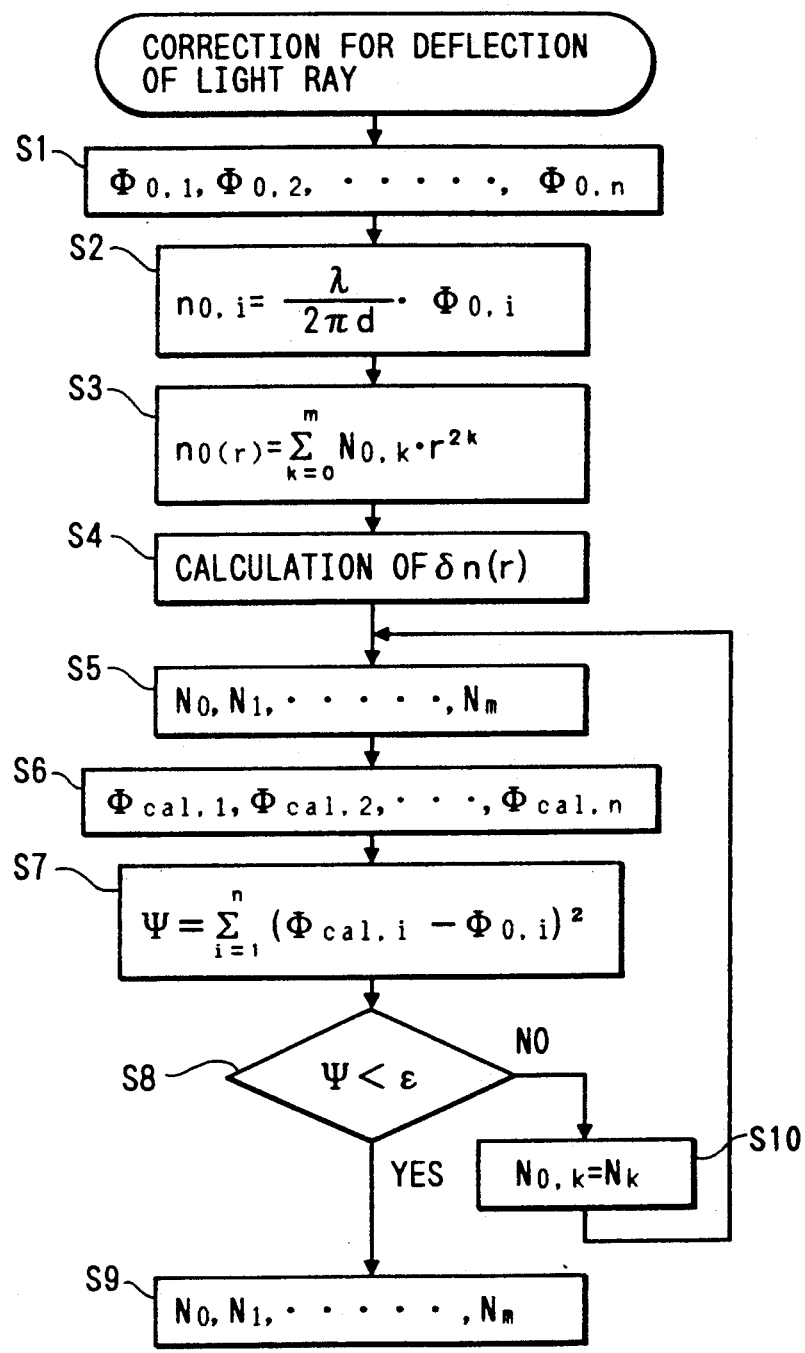
FIG. 3 is a flow chart showing the procedure of correction for deflection of data in the present invention.

Referring first to FIG. 1, prior to describing the embodiment, the function of the gradient index measuring apparatus according to the present invention will be explained.

In the case where an interferometer is utilized for measuring the gradient index of a sample, the phase distribution of wave fronts transmitted through the sample is measured and the resultant data of the phase distribution is converted to the gradient index. A ray of light, when transmitted through the sample, is deflected by the influence of the gradient index, but when the thickness of the sample is small and the influence of the deflection on the light ray is so slight that it can be neglected, a phase difference $\Delta\Phi$ and an index difference $\Delta n$ can be expressed by the linear relation $$\Delta n = (\Delta\Phi \, \lambda)/(2\pi d) \tag{1}$$

where d is the thickness of the sample, $\lambda$ is the wavelength of coherent light used for measurement, and the unit of the phase difference $\Delta\Phi$ is radian.

On the other hand, when the sample is thicker and the influence of the deflection cannot be neglected, the phase difference $\Delta\Phi$ and the index difference $\Delta n$ do not depend on the proportional relationship given by Eq. (1). Hence, the correction of the phase distribution data is required in which the influence of the deflection is taken into consideration. This correction is such that the wave front profile of light incident on the sample is regarded as already known and the deflection of the light is determined by a numerical calculation to derive the optimal distribution coefficient of the phase distribution data.

As mentioned above, even though the data were corrected with respect to the thickness of the sample, the measured phase distribution data would include a slightly asymmetrical error produced about the center of the sample due to the asymmetry of the gradient index of the sample. Further, in the use of the phase distribution data converted to the gradient index, even though the influence of the deflection on the light ray within the sample were numerically corrected, the asymmetrical error could not be eliminated. It is therefore required that the measured phase distribution data are corrected, taking account of the asymmetry of the gradient index.

Thus, the measuring apparatus of the present invention, as shown in FIG. 1, is designed so that the measured phase distribution data are approximated to a polynomial by a least square method, an error component with the approximation is previously calculated, the resultant data are separated into an approximate component, namely, a symmetrical component, and an approximate error component, namely, an asymmetrical component, which are each converted to the gradient index, and then the converted values are added to find the gradient index. Thus, the correction of data of the approximate components results in improved convergency with a high degree of accuracy and allows the accuracy of measurement of the gradient index to be improved.

Since the approximate error component has a small value compared with the gradient index, the influence of the deflection on the light ray in the sample need not be taken into account and asymmetry $\delta n$ can be derived from asymmetry $\delta\Phi$ which is the approximate error component of the phase distribution data, by the simple linear reduced equation $$\delta n = (\delta\Phi \, \lambda)/(2\pi d) \tag{2}$$

For the methods of approximation and calculation of the measured data mentioned above, a gradient index n(r) in the gradient index lens can be generally expressed, in terms of even orders, by the polynomial $$n(r) = n_0 + n_1 r^2 + n_2 r^4 + \tag{3}$$

where r is a radial distance from the center of the lens, $n_0$ is the refractive index at the center of the lens, and $n_1, n_2, \ldots$ are index distribution coefficients.

Thus, the measured phase distribution data $\Delta\Phi$ is approximated to the polynomial of phase distribution coefficients $\phi_0, \phi_1, \phi_2, \ldots$, based on the least square method, given by $$\Delta\Phi(r) = \phi_0 + \phi_1 r^2 + \phi_2 r^4 + \tag{4}$$

In addition, Eq. (4) is converted to the polynomial of the gradient index n(r) of Eq. (3) by the reduced equation to find the refractive index $n_0$ and the index distribution coefficients $n_1, n_2, \ldots$ If the approximate error component $\delta\Phi$ where the phase distribution data are approximated by the least square method is converted to the error $\delta n$ of the gradient index by the reduced equation to find a positional distribution $\delta n(r)$ of the error $\delta n$, the asymmetry will be obtained with respect to the gradient index symmetrically produced about the center. When the phase distribution data $\Delta\Phi$ which is approximated by the least square method is expressed by Eq. (4), an accurate gradient index $n_{MEASURE}(r)$ is secured by adding the approximate error $\delta n(r)$ to the data and expressing the gradient index n(r) as $$n_{MEASURE}(r) = n_0 + n_1 r^2 + n_2 r^4 + \ldots + \delta n(r) \tag{5}$$

The distribution $\delta n(r)$ obtained here is asymmetrical in regard to the center of the lens. If the equation is approximated to the polynomial of a proper number of orders, for example, $a_0 + a_1 r^2 + a_2 r^4 + \ldots$, to which the gradient index n(r) is added, and ray tracing is performed by using the equation, this imaging performance of the lens can be discussed. Further, when the statistical data of the approximate error $\delta n(r)$, for example, RMS (Root Mean Square), P-V (Peak to Valley) values, etc., are calculated, the asymmetry can be found quantitatively.

Referring now to the drawings shown, the embodiment of the present invention will be explained below. FIG. 2 is a schematic view showing the optical system of a preferred embodiment of the present invention. In this figure, reference numeral 1 denotes a sample to be measured, having a gradient index and both surfaces ground into plane surfaces parallel to the direction of the gradient index, 2 a coherent light source such as a laser, 3 a beam expander for increasing a beam diameter, 4 a beam splitter, 5 a fixed planar reflecting mirror, 6 a piezoelectric element for slightly changing an optical path length, 7 a slightly displaceable planar reflecting mirror, 8 a beam splitter, 9 an imaging optical system, 10 a light-receiving element, and 11 a control/arithmetic circuit. A beam emitted from the light source 2 increases in its diameter by virtue of the beam expander 3 and is divided, by the beam splitter 4, into two components: one, after reflection from the planar reflecting mirror 5, is transmitted through the sample 1 and the other, reflected as reference light by the planar reflecting mirror 7, is combined with the light wave of the one component at the beam splitter 8 and interferes. Interference fringes thus produced are imaged on the light-receiving element 10 by the imaging optical system 9. The piezoelectric element 6 is controlled by the control/arithmetic circuit 11 and at the same time, a phase is calculated from data fetched from the light-receiving element 10 so that, from the phase value, the calculation for finding the gradient index is performed.

Next, reference is made to the calculation method of finding the gradient index and its asymmetry from the phase distribution data. Where the sample 1 is small in thickness and the light ray does not undergo the influence of the deflection in the sample 1, the phase distribution data detected from the light-receiving element 10 can be converted into the gradient index from the relation given by Eq. (1). In contrast to this, when the sample is thicker and the light ray is subjected to the influence of the deflection, it is necessary to correct the data by the procedure shown in the flow chart of FIG. 3.

This correction of the data is such that ray tracing in the sample is carried out by the numerical calculation and the least square method is used to minimize the difference between the calculated phase distribution data after the light emerges from the sample and the measured phase distribution data. In Step S1 of the diagram, the phase differences $\Phi_{0,1}, \Phi_{0,2}, \ldots, \Phi_{0,n}$ between the light at the exit surface of the sample, measured by the interferometer, and the reference light are measured. In Step S2, based on the assumption that the light is not deflected in the sample, the phase difference data are converted to the gradient index. In Step S3, the converted gradient index is approximated to the polynomial by the least square method, and a coefficient $N_{0,k}$ of the polynomial is set to an initial value for finding the optimal distribution coefficient by applying the least square method in Step S5. In Step S4, the approximate error $\delta n(r)$ brought through the least square method in Step S3 is previously calculated. In Step S5, an optimal distribution coefficient $N_k$ is chosen to minimize the square sum of the differences between the phase distribution data, after the light emerges from the sample, calculated based on the wave front contour of light of incidence regarded as already known, with the coefficient $N_{0,k}$ as the initial value, by the numerical calculation using a so-called linear least square method, and the measured phase distribution data. In Step S6, the distribution coefficient $N_k$ chosen in Step S5 is used to calculate phase distribution data $\Phi_{cal,1}, \Phi_{cal,2}, \ldots, \Phi_{cal,n}$ after emergence from the sample. In Step S7, the square sum of the differences between the phase distribution data calculated in Step S6 and those measured in Step S1 is calculated, which is taken as a tolerance $\Psi$. In Step S8, the determination is made as to whether the tolerance $\Psi$ decreases sufficiently. When the tolerance $\Psi$ is brought within a required tolerance $\epsilon$, the distribution coefficient $N_k$ resulting from the ray tracing is determined as a gradient index coefficient of the sample 1, and in Step S9, the correction of the data is completed. On the other hand, where the tolerance $\Psi$ is not brought within the required tolerance $\epsilon$, the initial value of the coefficient is changed to $N_{0,k} = N_k$ in Step S10 and then a series of procedures in Steps 5 to 8 is repeatedly performed until the tolerance $\Psi$ is brought within the required tolerance $\epsilon$.

Figure 4:
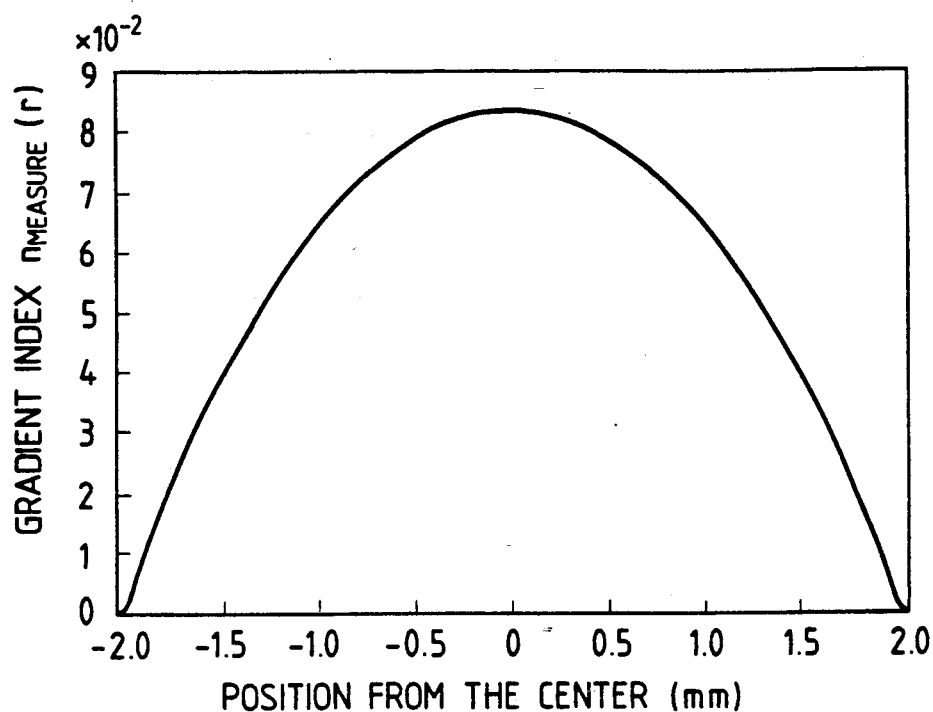
FIG. 4 is a view showing the result of measurement of the gradient index in the embodiment of the present invention.

FIG. 4 shows the result of measurement of the gradient index $n_{MEASURE}(r)$ in the embodiment in which as mentioned above, the phase distribution data measured by the interferometer are corrected for deflection and converted to the gradient index $\Delta n(r)$, to which the previously calculated approximate error distribution $\delta n$ is added. In the embodiment, the approximation is made as the gradient index equation by six terms up to ten orders. The gradient index coefficients in this case are listed in a Table. For the measurement in the use of the interferometer, the absolute value of the refractive index cannot be found and the coefficient $N_0$, arbitrarily set to measure the difference between the refractive indices, is omitted from the Table.

TABLE

| | |
|---|---|
| $N_1$ | $-1.8921 \times 10^{-2}$ |
| $N_2$ | $2.7487 \times 10^{-4}$ |
| $N_3$ | $-5.8858 \times 10^{-4}$ |
| $N_4$ | $2.0575 \times 10^{-4}$ |
| $N_5$ | $-2.8251 \times 10^{-5}$ |

Since the calculated value of the approximate error $\delta n(r)$ brought by the least square method in Step S4 is sufficiently small compared with the gradient index, the data need not be corrected even though the sample is large in thickness and it is necessary only to multiply the calculated value by $(d \lambda/2\pi)$.

Figure 5:
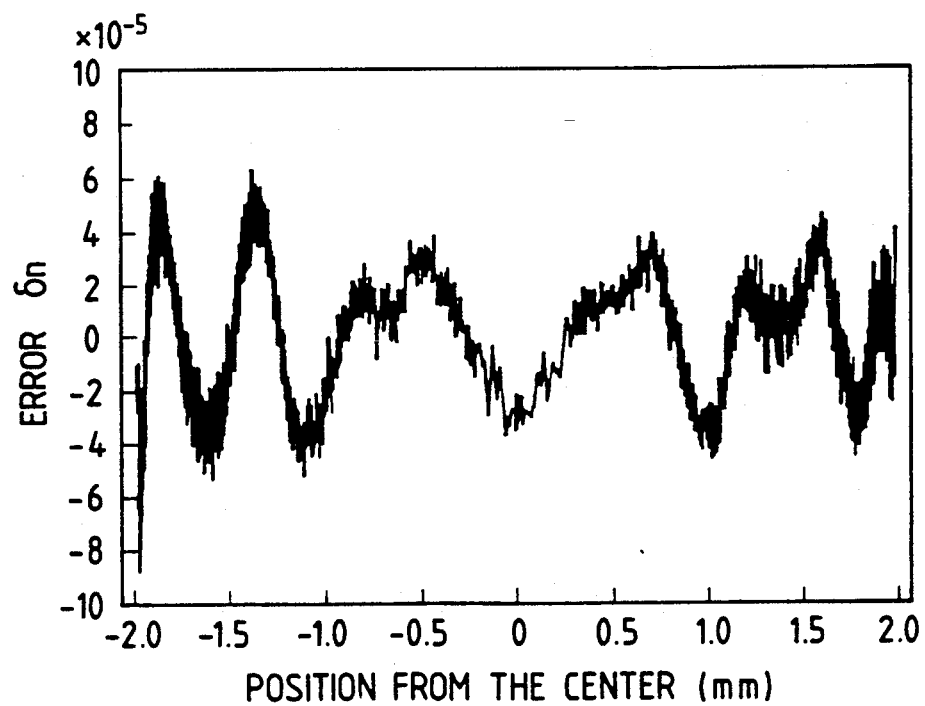
FIG. 5 is a view showing the asymmetry of the gradient index in the embodiment of the present invention.

FIG. 5 represents the difference between the measured value of the gradient index found by correcting the phase distribution data measured with the interferometer in view of the asymmetry, by the approximation of the least square method, and the value of the gradient index of only the approximate component, namely, the symmetrical component, found by approximating the phase distribution data through the least square method. In this figure, the symmetrical components contain higher order components than the order of the approximation, with respect to a center position "0" taken on the abscissa axis, and the asymmetrical components indicate the asymmetry of the gradient index of the sample.

The phase measurement of interference fringes is made by the use of a so-called fringe scanning method that, in regard to the optical path of one of light transmitted through the sample 1 and divided into two beams by the beam splitter 8, the planar reflecting mirror 7 disposed in the optical path is made to slightly change in $\lambda/M$ steps (where $\lambda$ is the wavelength to be measured and M is the number of divisions) by the piezoelectric element 6 and the phase is calculated from a change in intensity of the interference fringes at the measuring point in this case. When the intensity change of the interference fringes is represented by $I_0, I_1, \ldots, I_{M-1}$ at individual measuring points, a phase $\phi(x, y)$ at a given point is obtained from $$\phi(x, y) = \tag{6}$$
$$-\tan^{-1}\left\{ \left( \sum_{n=1}^{M-1} I_n \sin 2\pi \frac{n}{M} \right) \Big/ \left( \sum_{n=1}^{M-1} I_n \cos 2\pi \frac{n}{M} \right) \right\}$$

The fringe intensity at any point on the sample 1 is measured by the light-receiving element 10, for which a CCD is used to measure the entire sample surface. In the cases where the sample is too large to neglect the aberration of the imaging optical system 6 and where magnification is increased due to a high density of interference fringes and as a result, the entire sample surface cannot be measured in one operation, it is necessary only to make measurements while scanning the sample. Also, the phase measurement need not necessarily rely on the fringe scanning method and is available in other techniques, such as heterodyne, phase lock, and space fringe scan [Mitsuo Takeda: Appl. Phys. Opt. Soc., Optics, Vol. 13, p. 61 (1985)].

What is claimed is:

1. A gradient index measuring apparatus comprising:

means for generating at least a first light beam and a second light beam which have coherence;

a sample to be measured, placed on a first optical path along which said first light beam travels;

means for combining said first light beam traveling along said first optical path, transmitted through said sample, with said second light beam traveling along a second optical path; and arithmetic means for measuring interference fringes produced by the combination of said first light beam and said second light beam to calculate a gradient index of said sample from a measured value thereof, wherein said arithmetic means including, at least:

(a) means for approximating phase distribution data measured from said interference fringes to a phase distribution polynomial;

(b) means for separating said phase distribution data into an approximate component and an approximate error component;

(c) means for converting each of said approximate component and said approximate error component to the gradient index; and (d) means for adding a gradient index conversion value of said approximate component to another gradient index conversion value of said approximate error component.

2. An apparatus according to claim 1, further comprising means for measuring asymmetry of the gradient index of said sample from said approximate error component.

* * * * *